(12) United States Patent
Kübler (10) Patent No.: US 9,962,306 B2
(45) Date of Patent: May 8, 2018

(54) ARRANGEMENT FOR PREPARING AND POSITIONING PATIENTS TO BE TREATED AND/OR CARED FOR MEDICALLY

(71) Applicant: Guido Kübler GmbH, Bobingen (DE)

(72) Inventor: Guido Kübler, Bobingen (DE)

(73) Assignee: gKteso GmbH, Bobingen (DE)

( * ) Notice: Subject to any disclaimer, the term of this patent is extended or adjusted under 35 U.S.C. 154(b) by 391 days.

(21) Appl. No.: 14/765,591

(22) PCT Filed: Feb. 4, 2014

(86) PCT No.: PCT/EP2014/000292
§ 371 (c)(1),
(2) Date: Aug. 4, 2015

(87) PCT Pub. No.: WO2014/121919
PCT Pub. Date: Aug. 14, 2014

(65) Prior Publication Data
US 2015/0366733 A1 Dec. 24, 2015

(30) Foreign Application Priority Data

Feb. 6, 2013 (DE) .......................... 10 2013 002 183

(51) Int. Cl.
*A61G 13/12* (2006.01)
*A61G 13/00* (2006.01)
(Continued)

(52) U.S. Cl.
CPC ............ *A61G 13/00* (2013.01); *A61B 5/0046* (2013.01); *A61B 5/0555* (2013.01); *A61B 6/04* (2013.01); *A61B 5/6889* (2013.01)

(58) Field of Classification Search
CPC ...... A61G 13/00; A61G 13/12; A61G 13/121; A61G 13/1245; A61G 13/1235;
(Continued)

(56) References Cited

U.S. PATENT DOCUMENTS 5,259,011 A * 11/1993 Petro .................... A61B 6/04
378/20
5,490,297 A 2/1996 Bradcovich
(Continued)

FOREIGN PATENT DOCUMENTS

DE  102004048210 A1  1/2006
DE  102006057626 B3  12/2007
(Continued)

*Primary Examiner* — Ophelia A Hawthorne
(74) *Attorney, Agent, or Firm* — Michael Soderman (57) ABSTRACT

Arrangement for preparing and positioning patients to be treated and/or cared for medically, with at least two devices for preparing and positioning a patient in a preparation area and with at least one device for medically treating and/or caring for the patient in a treatment area. The preparation area and the treatment area are different and separated from each other by mobile or solid walls in order to prevent any visual openness to other patients. The preparation and positioning device has a dimensionally-stable base for receiving, preparing and positioning the patient and a linearly guided telescopic device that supports the dimensionally-stable base. The dimensionally-stable base can be relocated or transported together with the patient, who by the linearly guided telescopic device without floor guidance.

14 Claims, 11 Drawing Sheets

(51) Int. Cl.
*A61B 6/04* (2006.01)
*A61B 5/055* (2006.01)
*A61B 5/00* (2006.01)

(58) Field of Classification Search
CPC ....... A61B 5/0046; A61B 5/0555; A61B 6/04; A61B 5/6889; A47C 15/008
See application file for complete search history.

(56) References Cited

U.S. PATENT DOCUMENTS

| | | |
|---|---|---|
| 6,094,760 A | 8/2000 | Nonaka et al. |
| 7,560,698 B2 | 7/2009 | Rietzel |
| 2004/0001571 A1* | 1/2004 | Jahrling ................ A61B 6/032 378/209 |
| 2007/0135703 A1 | 6/2007 | Rietzel |
| 2009/0154645 A1 | 6/2009 | Lifshitz et al. |
| 2012/0174317 A1 | 7/2012 | Saracen |

FOREIGN PATENT DOCUMENTS

| | | |
|---|---|---|
| DE | 102006042572 A1 | 3/2008 |
| EP | 2135554 A1 | 12/2009 |

\* cited by examiner

ARRANGEMENT FOR PREPARING AND POSITIONING PATIENTS TO BE TREATED AND/OR CARED FOR MEDICALLY

CROSS-REFERENCE TO RELATED APPLICATIONS

This application is the U.S. national stage of International Application No. PCT/EP2014/000292 filed on Feb. 4, 2014, and claims the benefit thereof. The international application claims the benefit under 35 USC 119 of German Application No. 10 2013 002 183.9 filed on Feb. 6, 2013; all applications are incorporated by reference herein in their entirety.

BACKGROUND

The present invention relates to an arrangement for preparing and positioning patients to be treated and/or cared for medically.

Arrangements of this kind are generally known. For example, from U.S. Pat. No. 6,615,428 B1, U.S. Pat. No. 6,955,464 B1 or U.S. Pat. No. 7,216,383 B2 are known devices for preparing and positioning patients who are subjected to diagnostic examination by way of X-rays, computer tomography (CT), magnetic resonance imaging (MRI) or positron emission tomography (PET). These devices each consist of a patient bench which is directly assigned and, respectively, located next to or in front of the diagnostic appliance. Thereby, the patient bench is designed to be directly extendable to or into and, respectively, retractable from the diagnostic appliance. As an alternative, the patient bench may be designed to be extendable to or into and, respectively, retractable from a base aligned next to or in front of the diagnostic appliance, which however requires additional repositioning of the patient. The particular disadvantage of all these devices is the direct assignment and, respectively, allocation of the patient bench to or in the face of the diagnostic appliance. The patient bench and the diagnostic appliance are therefore set up in one and the same treatment room. Preparation and positioning of the patient to be treated and/or cared for medically and the actual medical treatment and/or care are therefore provided in immediate proximity of place and time. Preparation and positioning of a patient to be treated and/or cared for medically and the actual medical treatment and/or care of another patient can never be simultaneously and/or parallelly conducted. All these circumstances lead to extensive preparation phases, i.e., treatment intervals/downtimes and thus in general to high costs and time expenditures in medical treatment and/or care of the patient(s).

In addition, US 2009/0070936 A1, US 2012/0158017 A1, US 2012/0174317 A1 and U.S. Pat. No. 6,094,760 A describe computer-based robot systems for positioning patients at a device for medical treatment and/or care of patients. All of these robot systems have a number of considerable disadvantages. Without exception, these robot systems all have a very complex structural design and, as a consequence, all require extensive maintenance and servicing. In addition, these robot systems, owing to their mobility and high degree of flexibility, are extremely heavy and must be handled and operated by highly-qualified and experienced personnel. Owing to mobility and high degree of flexibility, there are simultaneously considerable risks of collision with the device for medical treatment and/or care of the patient, which at the same time poses a considerable risk of injury to patients, operating personnel and physicians. However, the most significant disadvantage of these robot systems in practice has shown to be the fact that these robot systems, as a principal rule, are assigned to a single device for medical treatment and/or care of the patient, i.e., they are positioned directly in the treatment room. Preparation and positioning of the patient to be treated and/or cared for medically and the actual medical treatment and/or care are consequently carried out in close range and dependency of time. Therefore, preparation and positioning of a patient to be treated and/or cared for medically and the actual medical treatment and/or care of another patient can never be simultaneously carried out. All this leads to extremely high manufacturing, operation and maintenance and repair costs arising generally from these robot systems on one side and extremely long preparation and, as a consequence, treatment intervals to the patients' detriment on the other side.

Finally, combined patient positioning and transport systems are known from U.S. Pat. No. 3,504,386 A, U.S. Pat. No. 5,475,884 A, U.S. Pat. No. 6,094,760 A, U.S. Pat. No. 5,259,011 A and US 2004/0001571 A1 or DE 101 27 210 A1, which comprise a patient bench and a transport cart to transport the patient bench with the patient. These patient positioning and transport systems in practice have all proved oneselves to be severely disadvantageous. For example, automated or even partially automated transport from a preparation room to a treatment room or vice versa or to another treatment room is not possible. In addition, simple transport between preparation room and treatment room is also excluded. Transport carts, owing to their size and weight including the weight of the patient to be transported, are usually very difficult to handle. This is the more true if there are ramps, hallway corners or similar between preparation room and treatment room. Transport here requires more personnel, i.e., at least one additional person, which in return leads to additional need for investment of time and money for the actual transport process. Not at least resulting therefrom in the transport process the risk of collision in transport alleys between preparation room and treatment room is extremely high, even if two persons are assigned to handling the transport cart. In addition, the transport process cannot be conducted irrespective of floor conditions to be locally met and thus without any vibrations at all. Such collisions and/or vibrations in turn have considerable negative effects upon the prepared and positioned patient in such respect that the preparation conducted in the preparation room and exactly set and defined positioning of the patient are considerably impaired or even neutralized and consequently must be repeated in the treatment room after the transport process has been completed. Finally, these types of patient positioning and transport systems are also associated with considerable problems due to the required relocation or reposition of the patient from the patient bench to the table for medical treatment and/or care. Even such a relocation will also have considerable negative effects in such respect that the preparations conducted in the preparation room and exactly set and defined positioning of the patient are considerably impaired or even neutralized, such that a preparation and positioning of the patient must be repeated or at least be additionally verified in the treatment room.

SUMMARY

The object of the present invention is therefore to provide an arrangement and/or device for preparing and positioning of patients to be treated and/or cared for medically, by means of which the aforementioned disadvantages can be prevented, which is therefore enabling simultaneous and/or parallel preparation and positioning of patients followed by treatment and/or medical care, while at the same time being in simple, compact and reliable constructional design, to a large extent being automated, in addition being easily, conveniently and safely used for patients, operating personnel and physicians, and finally to contribute considerably to reducing costs for treatment and/or care of patients.

DETAILED DESCRIPTION

This object is achieved in a surprisingly simple manner by the features of claim 1.

By means of the embodiment of the arrangement and/or device according to the invention for preparing and positioning patients to be treated and/or cared for medically, comprising at least two devices for preparing and positioning a patient in a preparation area and comprising at least one device for medically treating and/or caring for the patient in a treatment area, wherein the preparation area and the treatment area are different and are spatially separated and/or apart from each other and are separated from each other by mobile or solid walls in order to prevent any visual openness to other patients, with the at least one preparation and positioning device comprises a dimensionally-stable base for receiving, preparing and positioning the patient in the preparation area and a linearly guided telescopic device, which supports the dimensionally-stable base, and with the dimensionally-stable base is relocable or transportable together with the patient, who has been prepared and positioned in the corresponding preparation area on the dimensionally-stable base, by the linearly guided telescopic device without floor guidance and vibration-free from the corresponding preparation area to the at least one treatment and/or care device in the treatment area, and vice versa, a simultaneous and/or parallel preparation and positioning and subsequent treatment and/or care of patients is enabled. Besides, this allows for a much more efficient utilization rate of the medical facilities and/or devices and appliances to treat and/or care for patients and, consequently, a considerable increase of the number of patients to be treated and/or cared for medically per time unit. In addition, this enables a simple, compact and reliable constructional design of the arrangement according to the invention. Not at least resulting therefrom the constructional design of the arrangement according to the invention has minimum maintenance requirements. Another asset is the almost automated transport of the patient from the preparation area to a treatment area and back again to the preparation area or another treatment area, which in addition is particularly simple and easy to handle, also without any personnel being required. There is absolutely no risk of collision and/or injury to patients, staff and physicians owing to the linear movement schematics and automation. The transport process itself is not subject to collisions. In addition, the transport process is preferably not floor-guided and, as a consequence, is not impaired by any vibrations possibly caused by floor unevenness. Any preparations conducted in the preparation area and exactly set and defined positioning of the patient on the base is retained without any alterations. Finally, with the arrangement according to the invention any relocation or repositioning the patient is necessary. Both will render superfluous any renewed preparation and positioning of the patient, however at least any additional review of this. To the contrary, medical treatment and/or care for the patient may begin immediately after transport to the treatment area. As a consequence, by an arrangement according a considerable reduction of manufacturing, operational and maintenance costs as well as repair costs and reduction of required time as well as personnel and overhead costs in total for treatment and/or care of patients are reached.

Further advantageous details of the arrangement according to the invention are described in claims 2 to 14.

The features of claim 2 are particularly advantageous, according to which the at least two preparation and positioning devices and the at least one treatment and/or care device are in linear position to each other, which allows them to be moved towards and away from each other in a straight line.

In a preferential arrangement according to the invention, the at least two preparation and positioning devices according to claim 3 is positioned between two or more treatment and/or care devices.

In this context, two or more preparation and positioning devices according to claim 4 may very advantageously be arranged parallel to each other.

As an alternative or in cumulative manner, two or more preparation and positioning devices according to claim 5 may just as well and in advantageous manner essentially be arranged in a semicircle or in a circle next to each other around the at least one treatment and/or care device.

In addition, it is also provided according to the invention that two or more treatment and/or care devices according to claim 6 are arranged parallel to each other and/or one behind the other and/or in staggered arrangement.

The constructive characteristics according to claim 7 are particularly advantageous. Accordingly, the at least two preparation and positioning devices are designed such that the dimensionally-stable base supported by the linearly guided telescopic device of the at least two preparation and positioning devices are fully automatically moveable from the preparation area to the treatment area, and vice versa.

The features of claim 8 are particularly advantageous, namely in that the linearly guided telescopic device of the at least two preparation and positioning devices is actuable by electric motor and/or pneumatics and/or hydraulics. Actuation by electric motor is principally preferred. It may however be advantageous, as alternative or in cumulative form, to provide for actuation by pneumatics and/or hydraulics if this appears recommendable due to the particular situation or circumstances. Actuation by pneumatics or hydraulics might be advantageous, for example, if a diagnostic appliance in form of X-rays, computer tomography (CT), magnetic resonance imaging (MRI) or positron emission tomography (PET) is used as device for medical treatment and/or care for the patient.

In accordance with claim 9, the invention advantageously provides that the linearly guided telescopic device of the at least two preparation and positioning devices is entirely or partially supportable and guidable on a basis or foundation.

Expediently, the dimensionally-stable base and the linearly guided telescopic device of the at least two preparation and positioning devices according to claim 10 are inseparably bonded or connected to each other.

In an alternative embodiment of the invention, it is possible that the dimensionally-stable base and the linearly guided telescopic device of the at least two preparation and positioning devices according to claim 11 are separably coupled or connected with each other and the dimensionally-stable base is designed such that it is placeable by the linearly guided telescopic device on a supporting or bearing table of the at least one treatment and/or care device and is separably receivable and supported by the supporting or bearing table.

In a preferential embodiment, the dimensionally-stable base and the linearly guided telescopic device of the at least two preparation and positioning devices according to the features of claim 12 are designed relatively rotatable to each other.

As an alternative or in cumulative manner, the features of claim 13 according to the invention may be of advantage, according to which the dimensionally-stable base of the at least two preparation and positioning devices and the supporting or bearing table of the at least one treatment and/or care device are designed relatively rotatably to each other and/or the supporting or bearing table of the at least one treatment and/or care device and a base or foundation supporting the supporting or bearing table of the at least one treatment and/or care device are designed relatively rotatable to each other.

Finally, it is still part of the invention according to claim 14 to design the preparation and positioning devices identically to each other and/or to design the treatment and/or care devices identically or differently to each other.

BRIEF DESCRIPTION OF THE DRAWINGS

Further features, advantages and details of the invention are contained in the following description of a preferred embodiment of the invention, and in connection with the drawings. The drawings are as follows.

DETAILED DESCRIPTION OF THE PREFERRED EMBODIMENTS

In the following description of various embodiments of an arrangement 10 according to the invention, similar components that correspond to each other are each provided with identical reference characters.

The arrangement 10 according to the invention is provided for preparing and positioning patients 12 to be treated and/or cared for medically.

The arrangement 10 according to the invention comprises at least one device 14 for preparing and positioning the patient 12 in a preparation area 16 or similar preparation room. The preparation area 16 may be similarly provided and/or used as a treatment recovery room or similar for recovering from medical treatment and/or for post-treatment care of the patient 12.

The arrangement 10 according to the invention furthermore comprises at least one device 18 for medical treatment and/or care of the patient 12 in a treatment area 20 or similar treatment room. The medical treatment and/or care device 18 may be designed, for example, in form of a diagnostic appliance for diagnostic examination by way of X-rays, computer tomography (CT), magnetic resonance imaging (MRI) or positron emission tomography (PET). It is also conceivable to design the medical treatment and/or care device 18, for example, as gantry or similar design for radiation therapy for the patient 12 or as operating room for operative or surgical intervention and/or for operating the patient 12. Any other combination thereof or any other treatment and/or care devices 18 are also possible in the arrangement 10 according to the invention.

In the arrangement 10 according to the invention, the preparation area 16 and the treatment area 20 differ from each other in their functions. In addition, the preparation area 16 and the treatment area 20 in the arrangement 10 according to the invention are also spatially separated and/or apart from each other. The preparation area 16 and the treatment area 20 may be arranged in a common room or building section and/or may be situated in a common room or building section. It must, however, be assured that the preparation area 16 and the treatment area 20 are to a large extent self-contained and/or are separated from each other by way of suitable measures, for example visual barriers such as mobile walls or partition curtains, etc., in order to assure privacy and prevent any visual openness to other patients. In a preferential embodiment, however, the preparation area 16 and the treatment area 20 are separate rooms or building sections and are separated from each other by way of solid walls, building walls, etc. The preparation area 16 and the treatment area 20 may be immediately adjacent to each other, i.e. may be located directly next to each other, or may be also distant from each other by other preparation and/or treatment areas 16, 20 being located between these.

The at least one preparation and positioning device 14 comprises a dimensionally-stable base 22 for receiving, preparing and positioning the patient 12 in the preparation area 16. The patient 12 is accommodated by the dimensionally-stable base 22 and/or is placed upon this base and is supported and braced by this base. Prior to medical treatment and/or care, the patient 12 is properly prepared and suitably positioned and aligned in accordance with the intended treatment and/or care measures. The dimension stability of the base 22 assures that the position once taken by the patient 12 may be retained and thus cannot be changed by external force unless the patient moves himself.

In addition, the at least one preparation and positioning device 14 has a linearly guided telescopic device 24, which supports the dimensionally-stable base 22. By way of the linearly guided telescopic device 24, the patient 12, who was prepared and positioned in the preparation area 16 on the dimensionally-stable base 22 and is supported by it in unchanged position, may be relocated and/or transported from the preparation area 16 to the at least one treatment and/or care device 18 in the treatment area 20, and vice versa.

FIGS. 1A to 1H show a first embodiment of the arrangement 10 according to the invention comprising a preparation and positioning device 14 and a medical treatment and/or care device 18. The one preparation and positioning device 14 and the one medical treatment and/or care device 18 are each located in a separate preparation area 16 or preparation room and treatment area 20 or treatment room.

The preparation and positioning device 14 and the treatment and/or care device 18 are in linear disposition to each other; they are thus essentially in straight alignment with each other.

The preparation and positioning device 14 has a dimensionally-stable base 22, which is provided for receiving, preparing and positioning of a patient 12 in the preparation area 16.

In addition, the preparation and positioning device 14 in inventive embodiment comprises a linearly guided telescopic device 24 which supports the dimensionally-stable base 22. The linearly guided telescopic device 24 serves to relocate and/or transport the patient 12, who was prepared and positioned in the preparation area 16 on the dimensionally-stable base 22, from the preparation area 16 to the treatment and/or care device 18 in the treatment area 20, and vice versa.

The linearly guided telescopic device 24 in the embodiment of the arrangement 10 according to the invention described in FIGS. 1A to 1H is partially supported upon and may be guided on a basis 26 or a foundation of the preparation area 16 and/or preparation room.

Thus partial support of the telescopic device 26 is preferably used if the arising forces and torques owing to the distances and room conditions of and/or between the preparation area 16 and the treatment area 20 are not significantly high. The partial support of the telescopic device 26 has the advantage that it assures an absolutely vibration-free transport of the patient 12 from the preparation area 16 to the treatment area 20, and vice versa, without providing for a high degree of dimensional and tolerance accuracy between the telescopic device 24 and the basis 26. Without being depicted in detail, a constructional modification thereof also allows the linearly guided telescopic device 24 to be entirely supported, guided and moved on the basis 26 or the foundation.

The preparation and positioning device 14 is preferably designed such that the dimensionally-stable base 22, which is supported by the linearly guided telescopic device 24, is transportable vibration-free and/or fully automatically from the preparation area 16 to the treatment area 20, and vice versa.

Without being explained or depicted in detail, the linearly guided telescopic device 24 is designed to be actuable by electric motor and/or pneumatics and/or hydraulics.

Figure 1A:
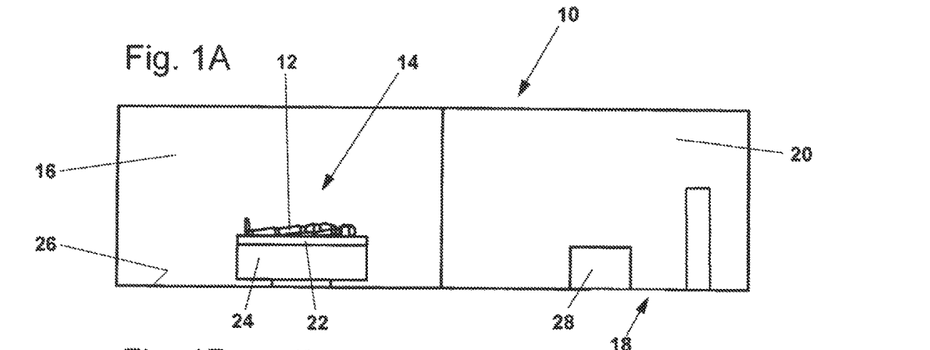
FIGS. 1A and 1B show a schematic lateral view and a top view of an embodiment of an arrangement according to the invention for preparation and positioning of patients to be treated and/or cared for medically in starting position.
Figure 1B:
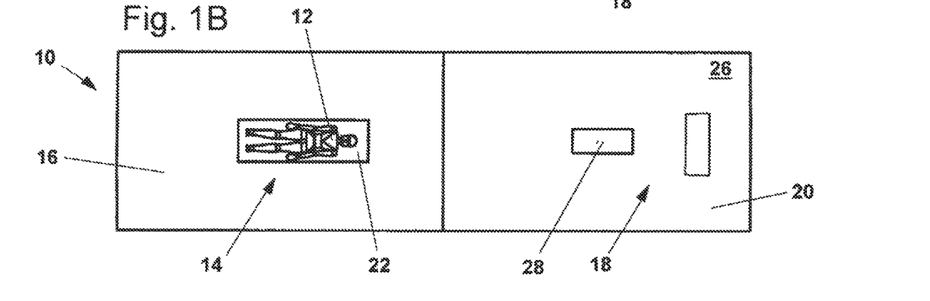

According to FIGS. 1A and 1B, the arrangement 10 according to the invention is in the starting position. The linearly guided telescopic device 24 is entirely retracted. The patient 12 is prepared and positioned on the dimensionally-stable base 22 in the preparation area 16.

Figure 1C:
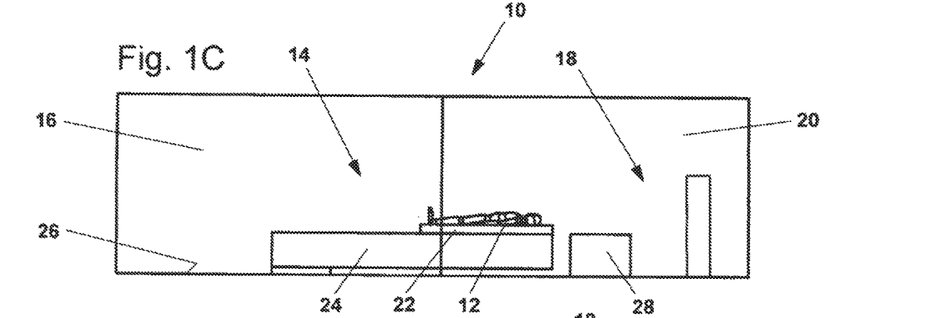
FIGS. 1C and 1D show a schematic lateral view and a top view of the embodiment of the arrangement according to the invention of FIGS. 1A and 1B in an intermediate position.
Figure 1D:
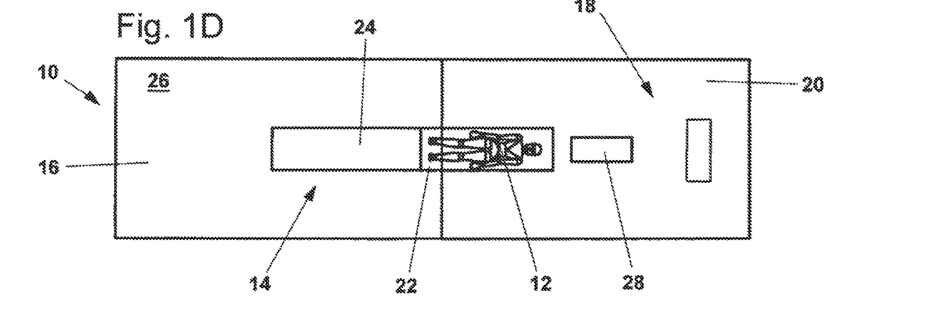

In FIGS. 1C and 1D, the arrangement 10 according to the invention is in an intermediate position. Thereby, the linearly guided telescopic device 24 is partially, as depicted here almost entirely, extended. The base 22 is just being relocated and/or transported from the preparation area 16 to the treatment area 20.

Figure 1E:
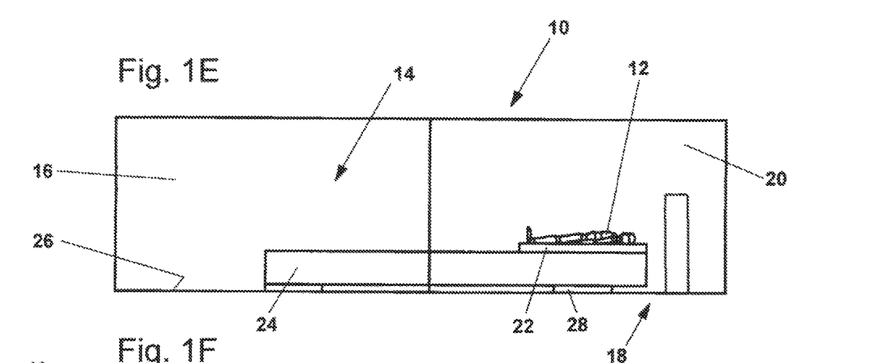
FIGS. 1E and 1F show a schematic lateral view and a top view of the embodiment of the arrangement according to the invention of FIGS. 1A and 1B in a terminal position or in another intermediate position.
Figure 1F:
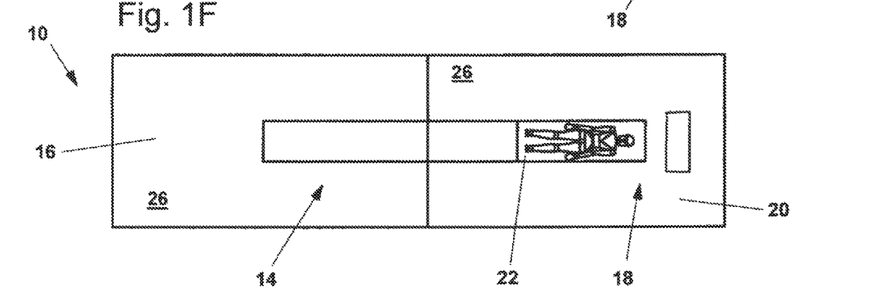
Figure 1G:
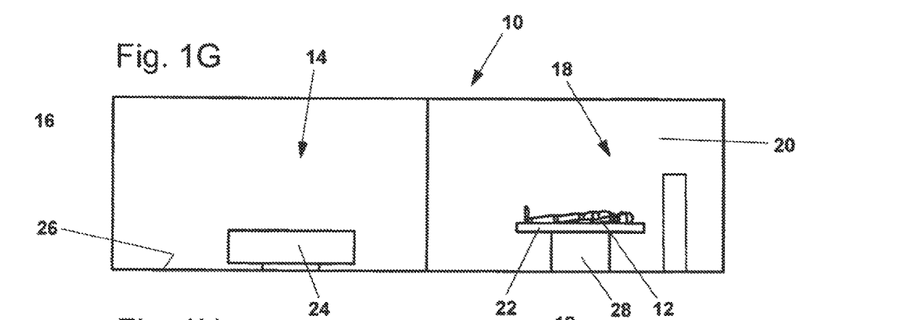
FIGS. 1G and 1H show a schematic lateral view and a top view of the embodiment of the arrangement according to the invention of FIGS. 1A and 1B in another terminal position.
Figure 1H:
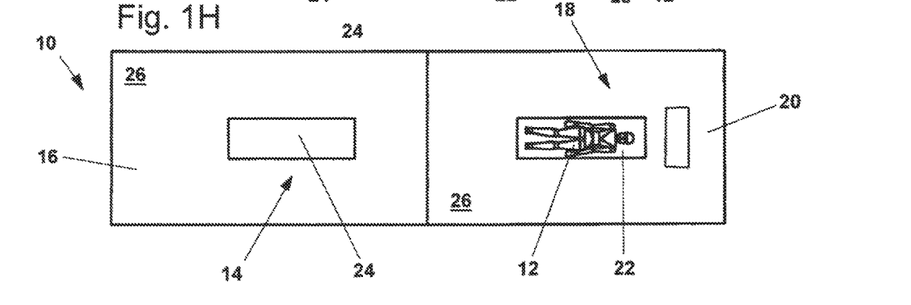

As is displayed in FIGS. 1E and 1F, the arrangement 10 according to the invention is in a terminal position or in another intermediate position. The linearly guided telescopic device 24 is entirely extended. The base 22 is entirely relocated and/or transported to the treatment area 20 and is directly allocated or assigned to the treatment and/or care device 18. The patient 12 on the base 22 is ready for the medical intervention and/or the medical care.

The dimensionally-stable base 22 and the linearly guided telescopic device 24 are expediently inseparably coupled or connected to each other. In accordance with FIGS. 1E and 1F, the linearly guided telescopic device 24 has reached its terminal position and is entirely extended.

To the contrary, the dimensionally-stable base 22 and the linearly guided telescopic device 24 may also be separably bonded to each other. In accordance with FIGS. 1G and 1H, this would allow to transfer the dimensionally-stable base 22 from the linearly guided telescopic device 24 to a supporting or bearing table 28 of the treatment and/or care device 18. The dimensionally-stable base 22 is separably placed upon and supported by the bearing table 28. According to FIGS. 1G and 1H, the linearly guided telescopic device 24 has thus merely adopted a different intermediate position and will then shuttle back from the treatment area 20 to the preparation area 16 in order to take another, in this case actual, terminal position.

Figure 2:
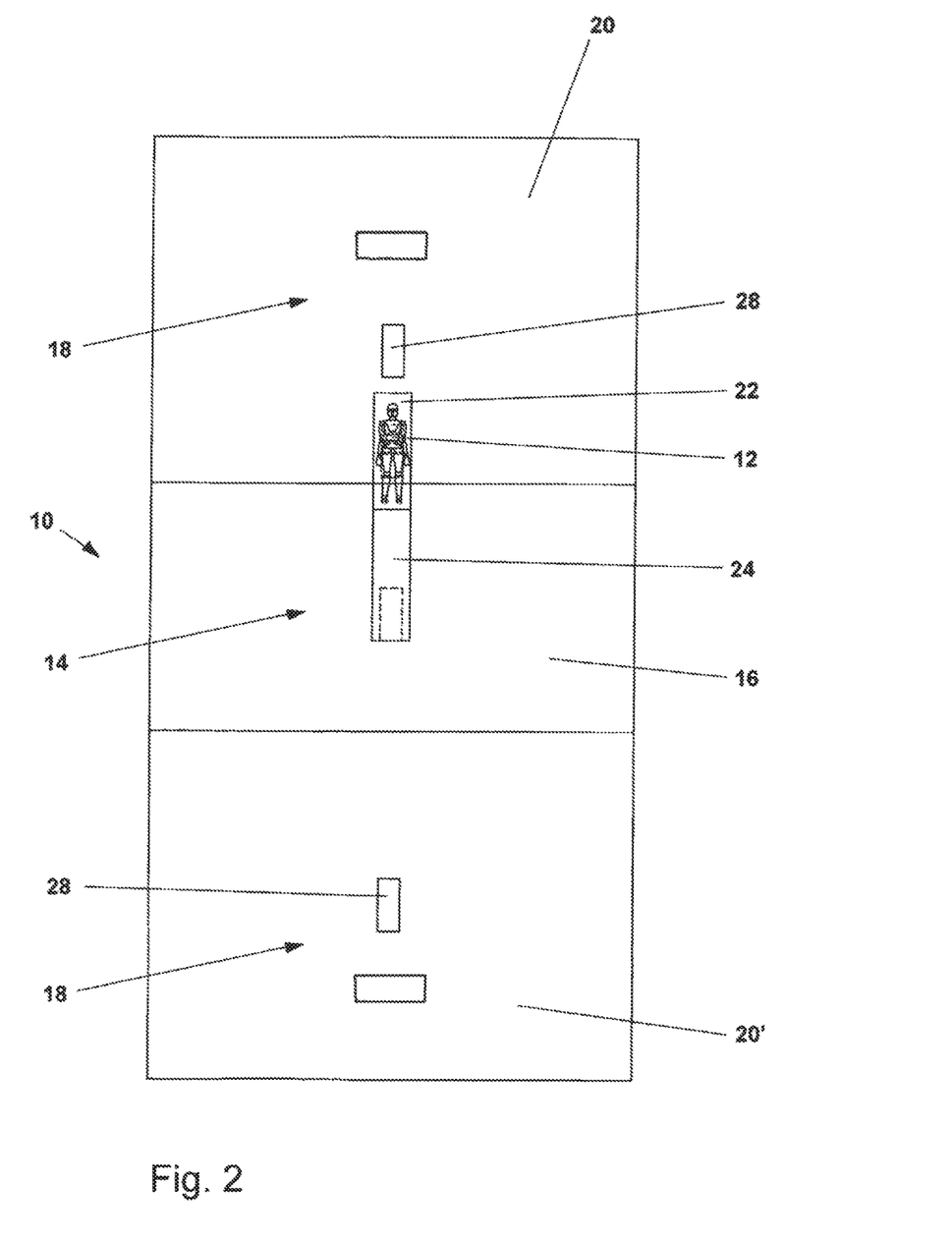
FIG. 2 shows an enlarged schematic top view of another embodiment of an arrangement according to the invention in an intermediate position.

FIG. 2 shows another exemplary embodiment of the arrangement 10 according to the invention.

The embodiment of the arrangement 10 according to FIG. 2 again comprises a preparation and positioning device 14 and two treatment and/or care devices 18, 18'. As a consequence, the arrangement 10 has another—i.e., second—treatment and/or care device 18'.

The preparation and positioning device 14 in this arrangement is located between the two treatment and/or care devices 18, 18'. The arrangement 10 according to the invention of FIG. 2 is in an intermediate position. The linearly guided telescopic device 24 is partially, i.e., almost entirely, extended. The base 22 is just being relocated and/or transported from the preparation area 16 to the treatment area 20.

This provides for the option to transfer the dimensionally-stable base 22 from the linearly guided telescopic device 24 to the supporting or bearing table 28 of the treatment and/or care device 18 and then to transport the linearly guided telescopic device 24 from the treatment area 20 back to the preparation area 16. During the medical treatment and/or medical care of this patient 12, a second patient 12 (not depicted) may then be prepared and positioned on the dimensionally-stable base 22 in the preparation area 16. This other patient 12 is then transported to the treatment and/or care device 18' with the dimensionally-stable base 22 by the linearly guided telescopic device 24, in order to conduct medical treatment and/or care to this other patient 12, i.e., simultaneously with the treatment and/or care of the patient 12 by the treatment and/or care device 18.

Figure 3A:
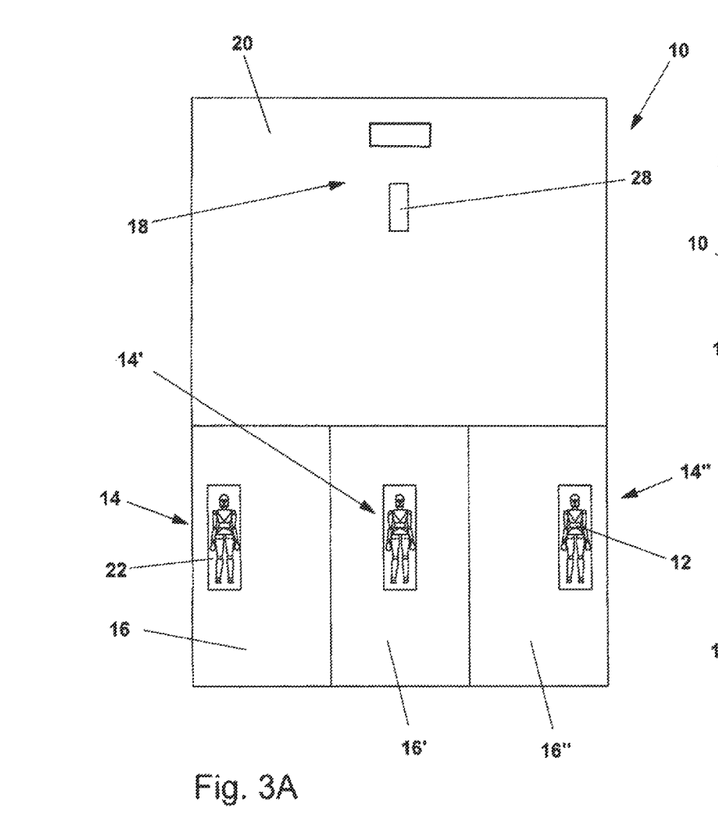
FIGS. 3A and 3B show schematic top views of yet another embodiment of an arrangement according to the invention in a starting position and an intermediate position.
Figure 3B:
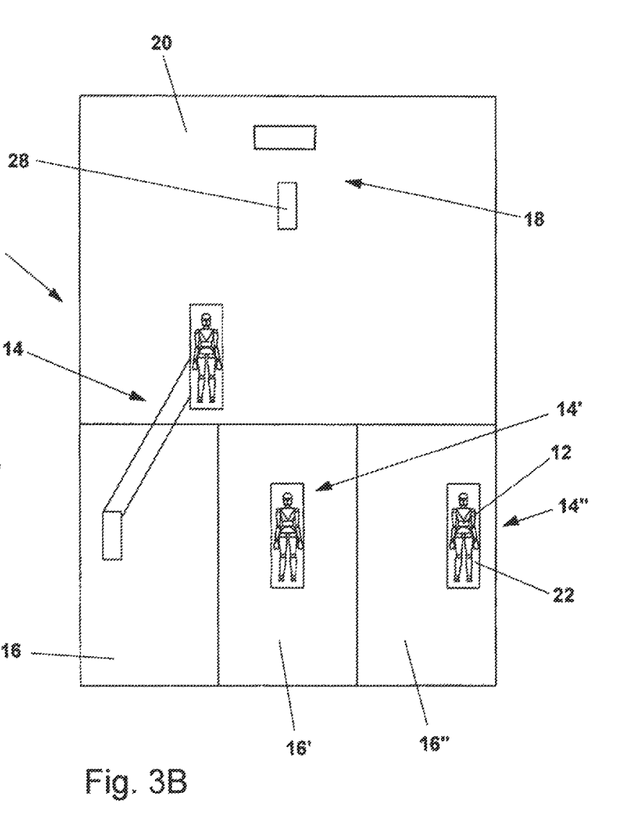

FIGS. 3A and 3B display yet another embodiment of the arrangement 10 according to the invention.

The embodiment of the arrangement 10 according to FIGS. 3A and 3B comprises a total of three preparation and positioning devices 14, 14', 14" and a treatment and/or care device 18.

The three preparation and positioning devices 14, 14', 14" are located parallel to each other. The patients 12 may thus be prepared and positioned on the dimensionally-stable bases 22 of the corresponding preparation and positioning device 14, 14', 14"; this may be done simultaneously, almost simultaneously or in a precisely defined staggered sequence.

As is displayed in FIG. 3B, the arrangement 10 according to the invention is in an intermediate position. The linearly guided telescopic device 24 of one (here: the left and/or upper one) of the three preparation and positioning devices 14, 14', 14" is partially extended. The base 22 is just being relocated and/or transported from the preparation area 16 to the treatment area 20.

In addition, the dimensionally-stable base 22 and the linearly guided telescopic device 24, without being depicted in detail, are preferably designed such that they are relatively rotatably to each other. If so desired, this provides for an option, for example, to carry out a translatory movement of the dimensionally-stable base 22. The movement of the base 22 is regularly consistent and at the same time defined in order to obtain a desired relative position between the dimensionally-stable base 22 and the linearly guided telescopic device 24 in the preparation area 16 on the one side as well as the dimensionally-stable base 22 and the assigned treatment and/or care device 18 and/or its supporting or bearing table 28 in the treatment area 20 on the other side.

In alternative or cumulative embodiment thereof, the dimensionally-stable base 22 and the supporting or bearing table 28 may be designed such that they are relatively rotatably to each other. It is also conceivable as alternative or cumulative embodiment thereof to design the supporting or bearing table 28 of the treatment and/or care device 18 and a basis 26 or foundation bracing the supporting or bearing table 28 of the at least one treatment and/or care device 18 such that they are relatively rotatably to each other.

Figure 4:
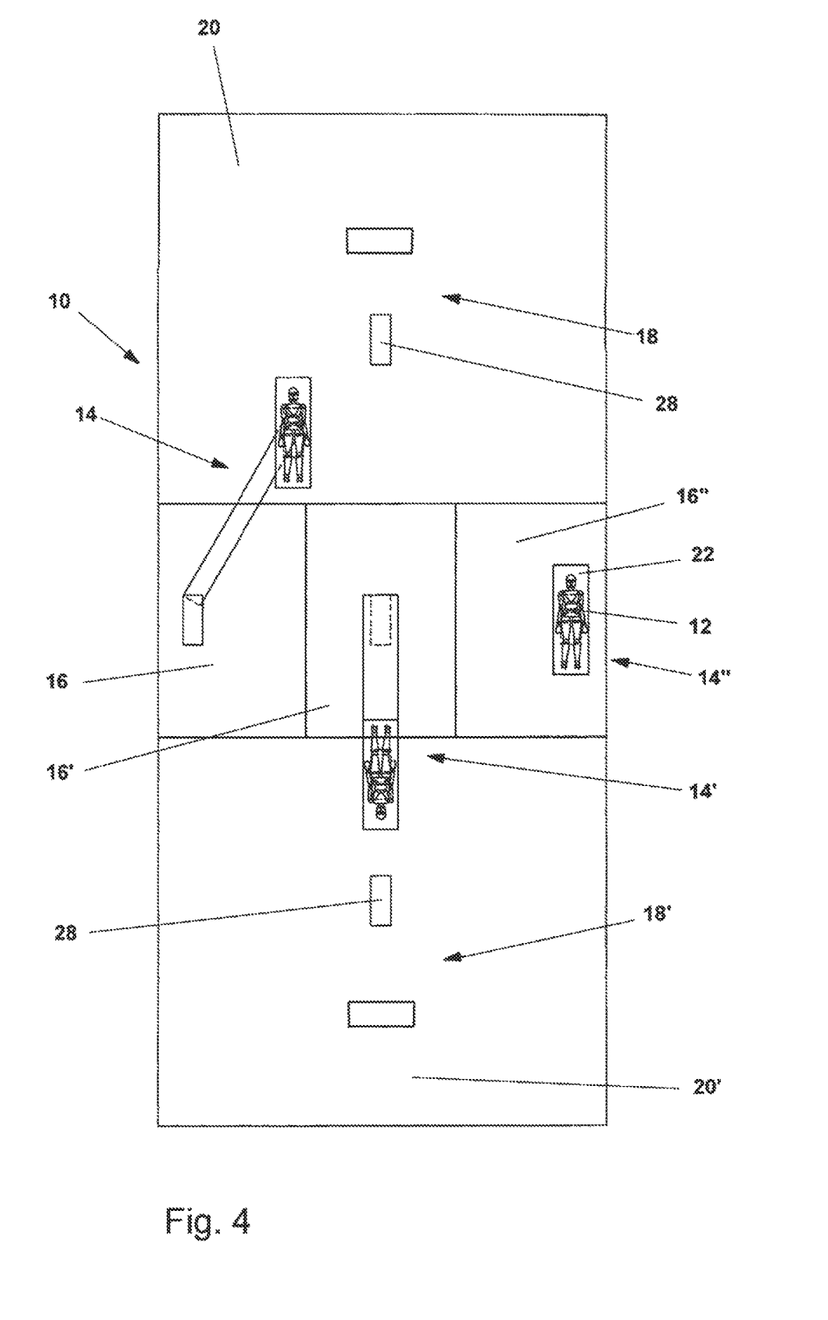
FIG. 4 shows a schematic top view of another embodiment of an arrangement according to the invention.

FIG. 4 displays another embodiment of the arrangement 10 according to the invention, which depicts a combination of the two embodiments of FIGS. 2 and 3A as well as 3B.

Accordingly, with the embodiment of the arrangement 10 of FIG. 4 a total of three preparation and positioning devices 14, 14', 14" and two treatment and/or care devices 18, 18' is suggested.

The three preparation and positioning devices 14, 14', 14" are located parallel to each other and between the two treatment and/or care devices 18, 18'. As is displayed in FIG. 4, the arrangement 10 according to the invention of FIG. 4 is in an intermediate position. Two linearly guided telescopic devices 24 are partially, i.e., almost entirely, extended. The bases 22 are just being relocated and/or transported from the preparation area 16 and/or 16' to the treatment area 20 and/or 20'.

Figure 5:
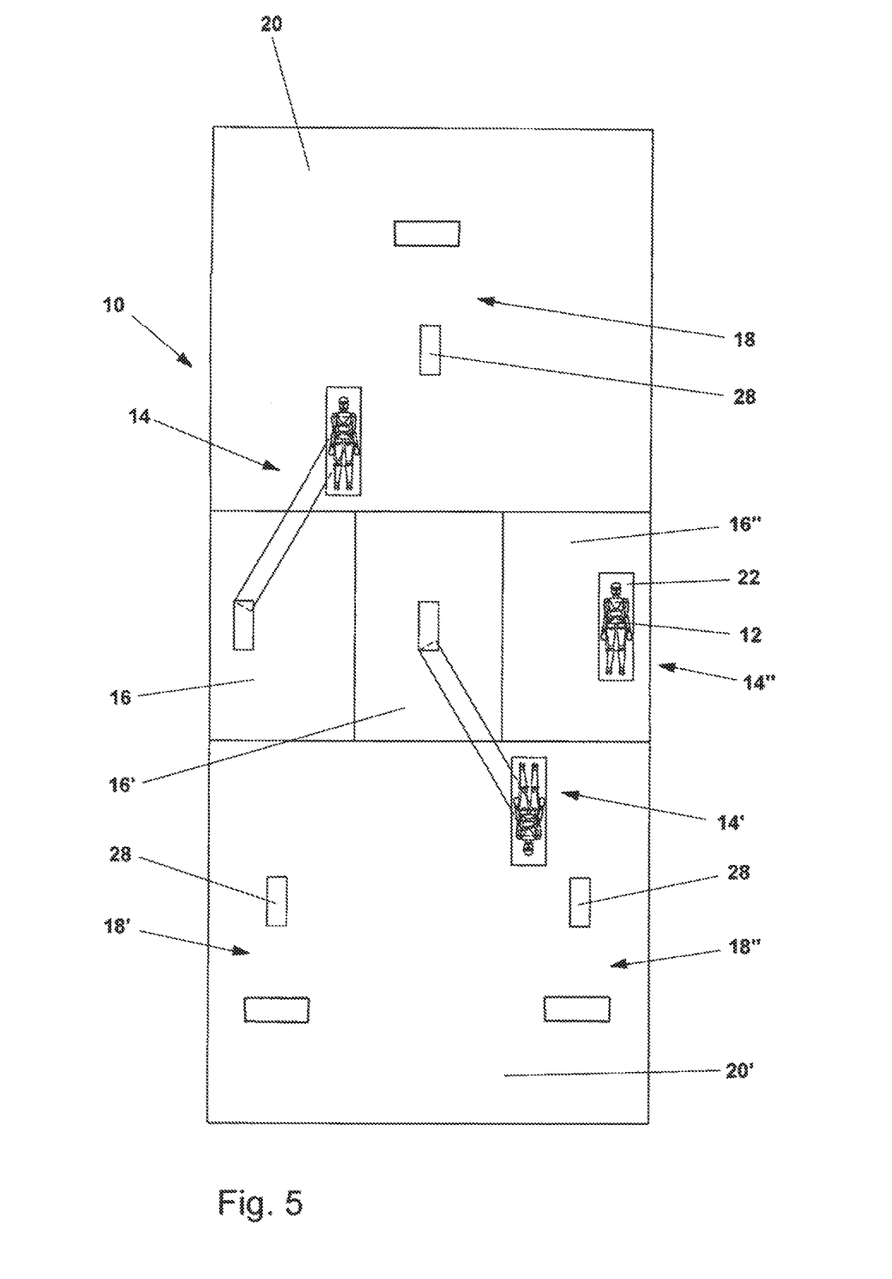
FIG. 5 shows a schematic top view of yet another embodiment of an arrangement according to the invention.
Figure 6:
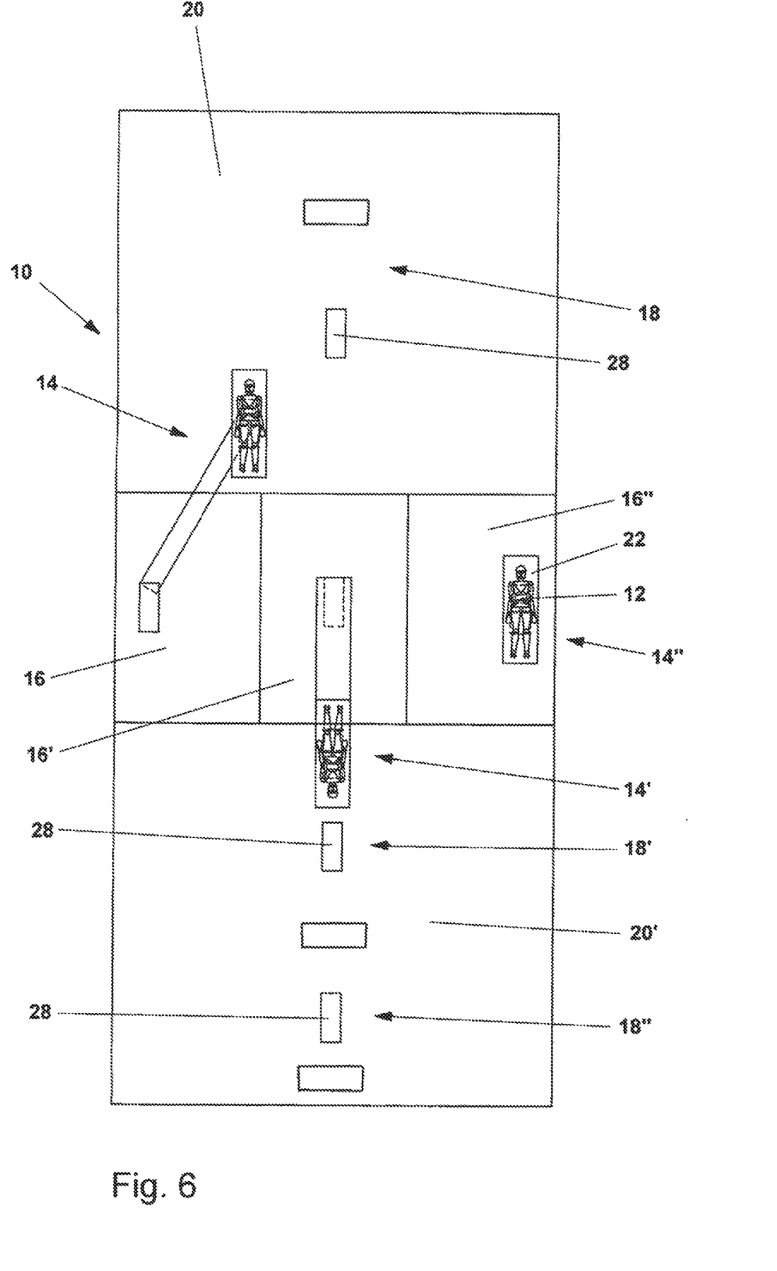
FIG. 6 shows a schematic top view of yet another embodiment of an arrangement according to the invention.
Figure 7:
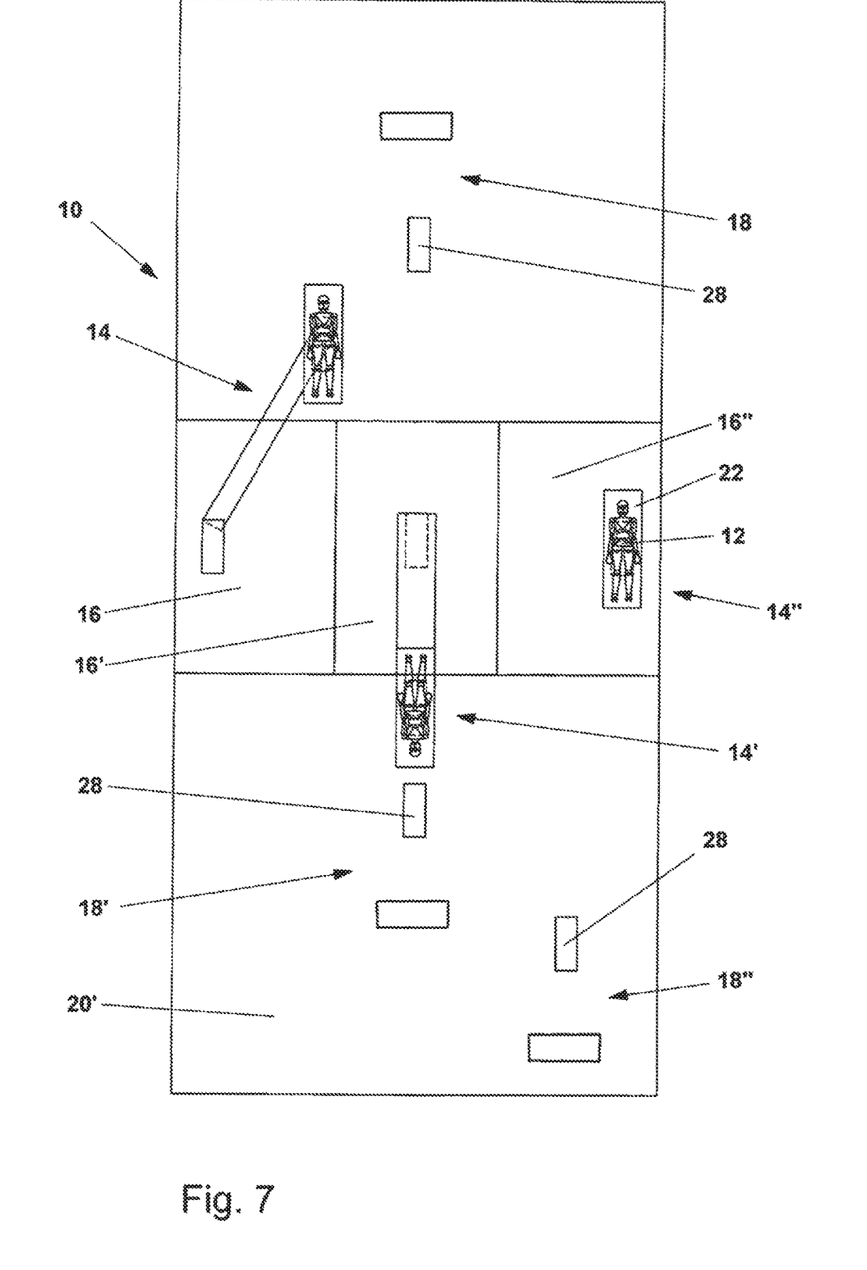
FIG. 7 shows a schematic top view of another modified embodiment of an arrangement according to the invention.

FIGS. 5 to 7 display yet other embodiments of the arrangement 10 according to the invention in modification of the embodiment according to FIG. 4.

In contrast to the embodiment of the arrangement 10 according to FIG. 4, in the treatment area 20' in the embodiment of the arrangement 10 of FIG. 5 two treatment and/or care devices 18', 18" are aligned parallel or essentially parallel to each other.

The embodiment of the arrangement 10 of FIG. 6 differs from the embodiment of the arrangement 10 according to FIG. 4 in that in the treatment area 20' two treatment and/or care devices 18', 18" are aligned one behind the other or essentially one behind the other.

In the embodiment of the arrangement 10 depicted in FIG. 7, in the treatment area 20' two treatment and/or care devices 18, 18' are in staggered alignment to each other.

Figure 8A:
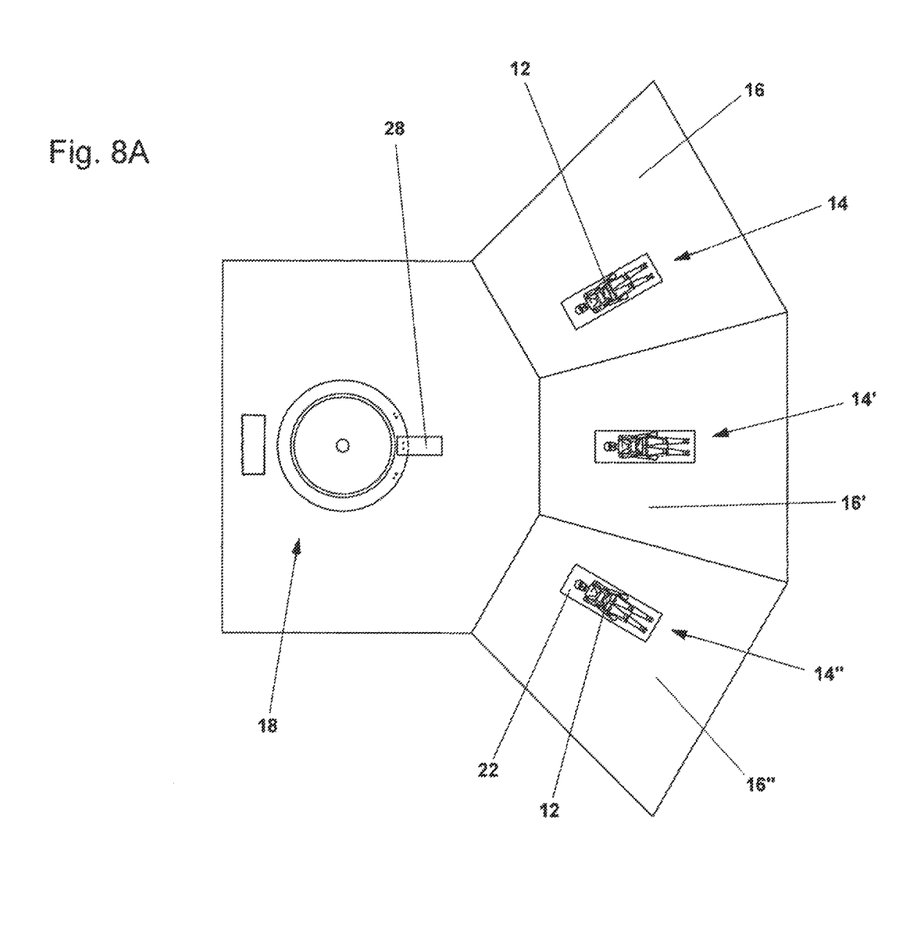
FIGS. 8A, 8B and 8C show schematic top views of another embodiment of an arrangement according to the invention in various positions, i.e., in starting, intermediate and terminal positions.
Figure 8B:
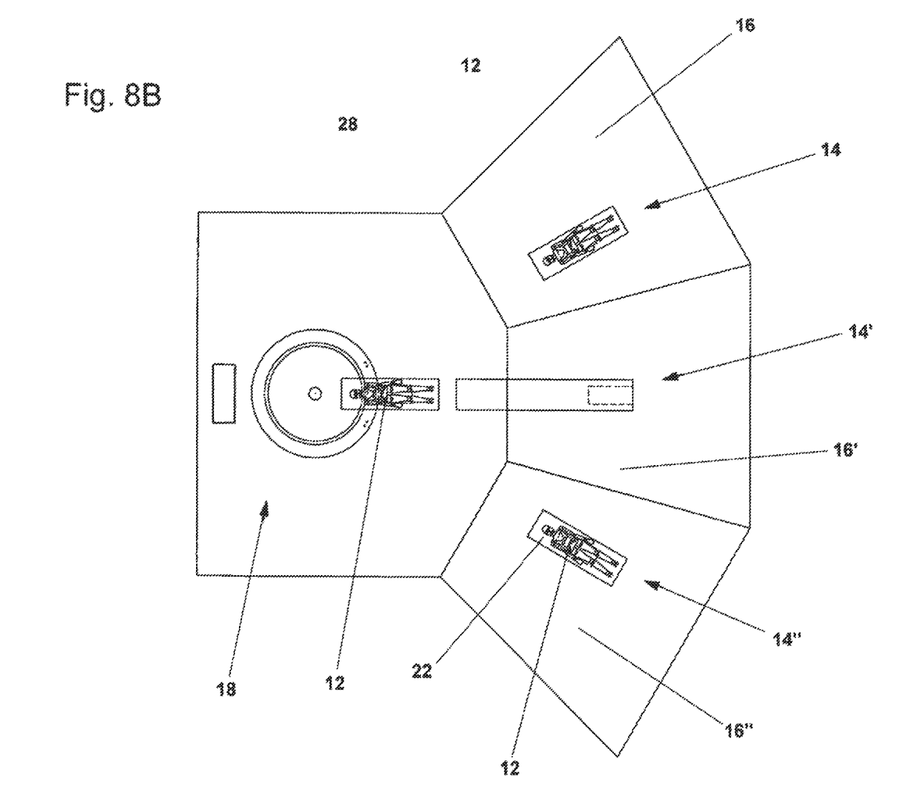
Figure 8C:
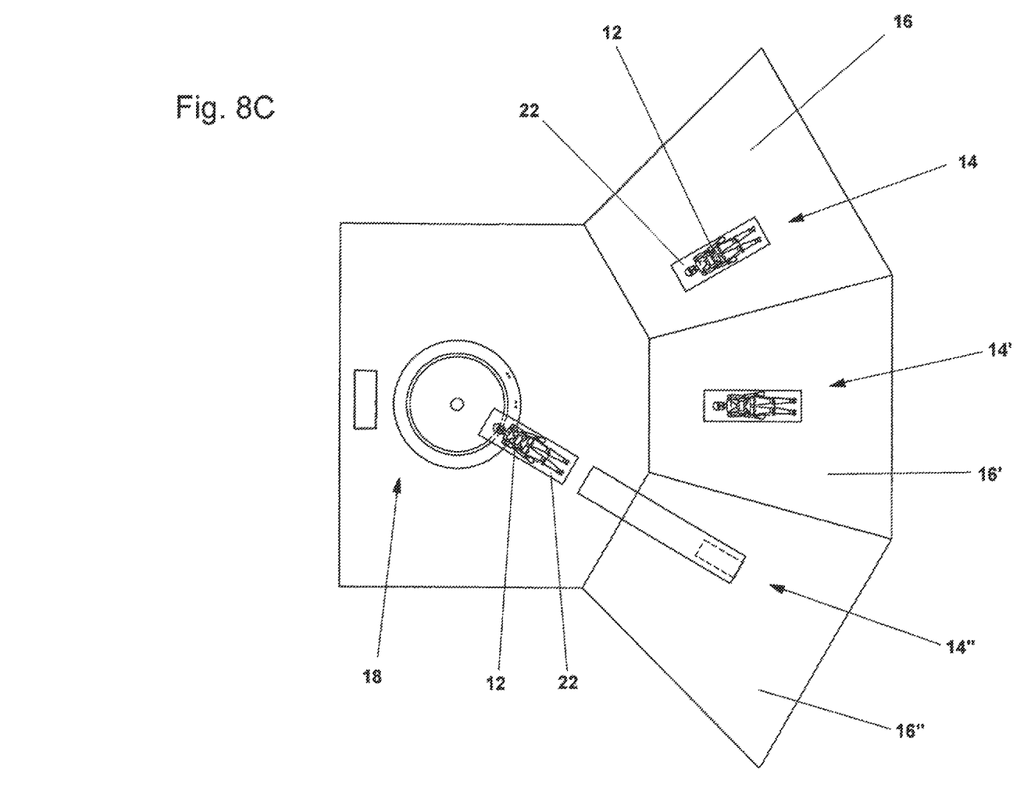

Finally, FIGS. 8A, 8B and 8C show yet another embodiment of the arrangement 10 according to the invention.

In the embodiment according to FIGS. 8A to 8C, there are two or more—in this present example a total of three—preparation and positioning devices 14, 14', 14" essentially arranged in a semi-circle next to each other around a treatment and/or care device 18. As may be taken from FIGS. 8B and 8C, the arrangement 10 according to the invention in FIGS. 8B and 8C is each in an intermediate position. Two linearly guided telescopic devices 24 are just being retracted into the terminal position after the dimensionally-stable base 24 with the patient 12 was placed on the supporting or bearing table 28 of the treatment and/or care device 18. The supporting or bearing table 28 is relatively rotated between the two positions according to FIGS. 8B and 8C.

The present invention is not restricted to the presented embodiments of the arrangement 10. It is, for example, also very conveniently possible to dispose the arrangement 10, in deviation from the aforestated embodiments according to FIGS. 8A to 8C, with two or more preparation and positioning devices 14, 14', 14" essentially in a circle next to each other, i.e., in a circular arrangement, around the at least one treatment and/or care device 18. Without being depicted in more detail, the preparation and positioning devices 14, 14', 14" may be identical to each other. The treatment and/or care devices 18, 18', 18" may be identical to each other or may differ from each other.

The invention claimed is:

1. An arrangement for preparing and positioning patients (12) to be treated and/or cared for medically, comprising at least two devices (14, 14', 14") for preparing and positioning a patient (12) in a preparation area (16, 16', 16") and comprising at least one device (18, 18', 18") for medically treating and/or caring for the patient (12) in a treatment area (20, 20', 20"), wherein the preparation area and the treatment area (16, 16', 16", 20, 20', 20") are different and are spatially separated from each other and are separated from each other by mobile or solid walls in order to prevent any visual openness to other patients, characterized in that the at least one preparation and positioning device (14, 14', 14") comprises a dimensionally-stable base (22) for receiving, preparing and positioning the patient (12) in the preparation area (16, 16', 16") and a linearly guided telescopic device (24), which supports the dimensionally-stable base (22), and that the dimensionally-stable base is relocatable or transportable together with the patient (12), who has been prepared and positioned in the corresponding preparation area (16, 16', 16") on the dimensionally-stable base (22), by the linearly guided telescopic device (24) without floor guidance and vibration-free from the preparation area (16, 16', 16") to the at least one treatment and/or care device (18, 18', 18") in the treatment area (20, 20', 20") and vice versa.

2. The arrangement according to claim 1, characterized in that the at least two preparation and positioning devices (14, 14', 14") and the at least one treatment and/or care device (18, 18', 18") are in linear position to each other.

3. The arrangement according to claim 1, characterized in that the at least two preparation and positioning devices (14, 14', 14") are positioned between two or more treatment and/or care devices (18, 18', 18").

4. The arrangement according to claim 1, characterized in that two or more preparation and positioning devices (14, 14', 14") are arranged parallel to each other.

5. The arrangement according to claim 1, characterized in that two or more preparation and positioning devices (14, 14', 14") essentially are arranged in a semicircle or in a circle next to each other around the at least one treatment and/or care device (18, 18', 18").

6. The arrangement according to claim 1, characterized in that two or more treatment and/or care devices (14, 14', 14")

are arranged parallel to each other and/or one behind the other and/or in staggered arrangement.

7. The arrangement according to claim 1, characterized in that the at least two preparation and positioning devices (14, 14', 14") are designed in such manner that the dimensionally-stable base (22) supported by the linearly guided telescopic device (24) of the at least two preparation and positioning devices (14, 14', 14") is fully automatically moveable from the preparation area (16, 16', 16") to the treatment area (20, 20', 20"), and vice versa.

8. The arrangement according to claim 1, characterized in that the linearly guided telescopic device (24) of the at least two preparation and positioning devices (14, 14', 14") is actuatable by electric motor and/or pneumatics and/or hydraulics.

9. The arrangement according to claim 1, characterized in that the linearly guided telescopic device (24) of the at least two preparation and positioning devices (14, 14', 14") is entirely or partially supportable and guidable on a basis (26) or foundation.

10. The arrangement according to claim 1, characterized in that the dimensionally-stable base (22) and the linearly guided telescopic device (24) of the at least two preparation and positioning devices (14, 14', 14") are inseparably coupled to each other.

11. The arrangement according to claim 1, characterized in that the dimensionally-stable base (22) and the linearly guided telescopic device (24) of the at least two preparation and positioning devices (14, 14', 14") are separably connected with each other and the dimensionally-stable base (22) is placeable by the linearly guided telescopic device (24) on a supporting or bearing table (28) of the at least one treatment and/or care device (18, 18', 18") and is separably receivable and supported by the supporting or bearing table (28).

12. The arrangement according to claim 1, characterized in that the dimensionally-stable base (22) and the linearly guided telescopic device (24) of the at least two preparation and positioning devices (14, 14', 14") are designed relatively rotatable to each other.

13. The arrangement according to claim 1, characterized in that the dimensionally-stable base (22) of the at least two preparation and positioning devices (14, 14', 14") and the supporting or bearing table (28) of the at least one treatment and/or care device (18, 18', 18") are designed relatively rotatable to each other and/or the supporting or bearing table (28) of the at least one treatment and/or care device (18, 18', 18") and a basis (26) or foundation supporting the supporting or bearing table (28) of the at least one treatment and/or care device (18, 18', 18") are designed relatively rotatable to each other.

14. The arrangement according to claim 1, characterized in that the preparation and positioning devices (14, 14', 14") are designed identically to each other and/or that the treatment and/or care devices (18, 18', 18") are designed identically or differently to each other.

* * * * *